(12) United States Patent
Holmes et al.

(10) Patent No.: US 8,438,956 B1
(45) Date of Patent: May 14, 2013

(54) TORQUE INDICATING DRIVER

(75) Inventors: Russell P. Holmes, Dover, MA (US);
William J. Silver, Grafton, MA (US)

(73) Assignee: Holmed Corporation, South Easton, MA (US)

( * ) Notice: Subject to any disclaimer, the term of this patent is extended or adjusted under 35 U.S.C. 154(b) by 0 days.

(21) Appl. No.: 12/256,958

(22) Filed: Oct. 23, 2008

Related U.S. Application Data (60) Provisional application No. 60/982,326, filed on Oct. 24, 2007.

(51) Int. Cl.
*B25B 23/14* (2006.01)
*B25B 23/159* (2006.01)

(52) U.S. Cl.
USPC ............................................. 81/467; 81/477

(58) Field of Classification Search ............. 81/467, 81/477, 478, 480; 606/104
See application file for complete search history.

(56) References Cited

U.S. PATENT DOCUMENTS

| | | | |
|---|---|---|---|
| 2,087,354 A * | 7/1937 | Muffly ......................... 267/155 |
| 2,205,510 A * | 6/1940 | Wolfram .......................... 81/477 |
| 2,400,978 A * | 5/1946 | Collins ....................... 73/862.21 |
| 2,464,372 A * | 3/1949 | Booth ........................ 73/862.21 |
| 3,069,903 A | 12/1962 | Larson |
| 3,564,955 A * | 2/1971 | Batchelder ................... 81/57.29 |
| 3,678,744 A | 7/1972 | Blattner |
| 3,832,916 A * | 9/1974 | Schoeps .......................... 81/477 |
| 4,238,978 A | 12/1980 | Leone |
| 5,048,381 A * | 9/1991 | Allen et al. ...................... 81/477 |
| 5,241,424 A * | 8/1993 | Watanabe ...................... 359/811 |
| 5,704,261 A | 1/1998 | Strauch et al. |
| 5,737,983 A | 4/1998 | Rennerfelt |
| 6,062,115 A | 5/2000 | Bares et al. |
| 6,571,646 B1 | 6/2003 | Truesdell |
| 6,575,042 B1 * | 6/2003 | Rinner ........................... 81/477 |
| 7,055,415 B1 | 6/2006 | Walsh et al. |
| 7,107,883 B2 | 9/2006 | Casutt |
| 7,243,581 B1 | 7/2007 | Gao |
| 7,255,703 B2 | 8/2007 | Mujwid et al. |
| 7,331,263 B2 * | 2/2008 | Erickson et al. ................ 81/467 |
| 2002/0120275 A1 | 8/2002 | Schmieding et al. |

* cited by examiner

*Primary Examiner* — Hadi Shakeri
(74) *Attorney, Agent, or Firm* — Cesari and McKenna, LLP (57) ABSTRACT

In one embodiment, a torque-indicating driver includes a handle configured to receive applied torque. One or more flat springs are coupled via a housing to the handle at their proximate ends. The one or more flat springs are configured to angularly deflect elastically in response to the applied torque. A hub is coupled to a distal end of the one or more flat springs, the hub having a torsion rod extending therefrom. The torsion rod is configured to apply torque to a load. An outer sleeve at least partially covers the housing. One or more plungers are affixed to the housing and configured to engage one or more holes or depressions disposed at predetermined locations in the outer sleeve. Engagement with the holes or depressions creates auditory and tactile feedback perceivable by a user of the torque-indicating driver to indicate when a particular torque level is reached.

17 Claims, 5 Drawing Sheets

TORQUE INDICATING DRIVER

RELATED APPLICATIONS

This application claims priority to U.S. Provisional Application No. 60/982,326, filed on Oct. 24, 2007, and entitled "Torque Indicating Driver." Such provisional application is incorporated by reference herein.

BACKGROUND

1. Technical Field

The present invention relates generally to surgical instruments and more specifically to torque-indicating drivers.

2. Background Information

In some surgical procedures, a surgeon may need to exert torque on a fastener or other object disposed within the human body. For example, orthopedists often treat a variety of different types of bone fractures and other skeletal conditions by installing bone screws in an affected area, to stabilize a bone, to attach constructs to a bone, or for other therapeutic purposes. When installing a bone screw into a bone, it is important that excessive torque not be applied. Excessive torque may "strip" threads in a bone, or may damage the bone screw itself. Certain bone screws that are made from easily deformable bioabsorbable materials may be particularly susceptible to damage. Due to the potential complications that can result from damaged caused from excessive torque, it is quite important that a surgeon measure the amount of torque he or she applies.

A variety of different types of torque-indicating drivers exist for applying measured amounts of torque. Some torque-indicating drivers employ a torsion rod. In such drivers, the torsion rod is generally coupled at one end to a bit that engages a load, and at the other end to a handle where torque is applied. Applied torque is transmitted to the bit via the torsion rod, which angularly deflects in response to the torque. The deflection of the torsion rod is measured by comparing markings on the torsion rod with marking on the handle.

While torsion rod-based torque-indicating drivers are relatively simple and easy to manufacture, they suffer some shortcomings. For example, they are often unsuited for high-torque applications, as many torsion rods may not withstand such torque levels, or may not accurately measure torque at such torque levels. High torque levels may be needed for certain types of fasteners used in some surgical procedures.

Other types of existing torque-indicating drivers may employ one or more substantially rectangular plate springs, or one or more helical springs, rather than a torsion rod. Angular deflection of the springs is measured with markings, similar to in torsion rod-based designs. While plate springs and helical springs are often capable of withstanding higher levels of torque than torsion rods, they typically add bulk and thickness to the shaft of a torque-indicating driver. Accordingly, torque-indicating drivers that employ springs are generally unsuitable for use in confined spaces, for example, in the confined surgical space of a minimally invasive surgical procedure.

Further, existing torque-indicating drivers do not always well indicate the amount of torque that is applied. As discussed above, such instruments generally rely on indicator markings. Such markings are typically only visible from a certain perspective, for example, from directly above the driver, or from the side of the driver. During a surgical procedure, it may be difficult for a surgeon position him or herself in the best viewing location to view the markings. In some cases, sight lines may be obstructed by other instruments, or other medical personnel involved in the procedure, thus making it difficult to view the markings and measure the torque that is being applied.

Further, it is often difficult to adjust or calibrate many existing torque-indicating drivers during manufacture. Small variations may exist in the torsional properties of the components of a driver. Therefore, it may be desirable to make adjustments to a driver before it is delivered to a customer, to ensure it accurately measures torque. However, many existing drivers lack a simply yet effective mechanism for making such adjustments.

Accordingly, there is a need for an improved torque-indicating driver that overcomes the shortcoming of prior designs.

SUMMARY

In an illustrative embodiment, a new torque-indicating driver combines both flat torsion springs and a torsion rod to achieve a driver that can used at high torque levels yet still has a shaft that is quite narrow. The torque-indicating driver includes a handle coupled to a cylindrical housing. One or more flat torsion springs (or simply "flat springs") are attached to the housing, for example, by insertion into slots, which stabilize the springs and prevent rotation of their proximate ends. The springs are adapted to absorb torsional forces, angularly deflecting in response to the forces, while not plastically bending.

The flat springs are affixed to a hub at their distal ends, for example, by insertion into slots arranged in the hub. The hub is coupled to, or may be an integral part of, a torsion rod, which has a bit, socket or other member disposed at its distal tip for imparting torque on a load, for example, a fastener, such as a bone screw or a nut. As the flat springs absorb some torsional forces, the torsion rod is subject to more moderate forces than in previous implementations lacking flat springs. As such, the torsion rod may be constructed to have a quite narrow diameter, yet the driver may still be used at high torque levels.

In some configurations, an outer sleeve is positioned over the hub and extends upwards to enclose the flat springs and a portion of the housing. The outer sleeve is rigidly fixed to the hub and torsion rod, yet allowed to rotate independently of the housing and handle. One or more indicators extend downward from the housing over a portion of the outer sleeve. This portion of the outer sleeve is preferably marked with torque-indicating markings. The markings may include a centerline indicating substantially zero incident torque, flanked by torque-indicating lines and warning zones indicating, respectively, when a torque limit is reached and exceeded. In one example implementation, a pair of indicators may be positioned on opposing sides of the housing, each indicator employed with bidirectional markings to permit measurement of torque in clockwise or counter-clockwise directions.

In addition to visual indication, in some implementations, the driver may provide auditory and/or vibrational feedback. In one implementation, one or more ball-nose spring plungers, each comprising a spring-loaded ball bearing retained by a hold down rim, may be disposed in the housing. A ball bearing rides upon the inner surface of the outer sleeve until it encounters a hole or depression, positioned at a predetermined location in the housing coinciding with a particular torque level. The ball bearing then engages the hole or depression, becoming partially disposed therein. This results in an audible "click" that may be perceived by a surgeon or other user. Further, a vibration is produced when the ball engages the hole or depression, which may be felt through the handle by the surgeon or other user.

In implementations that employ a plunger, fine calibration of the driver may be made by varying properties of the plunger, for example, the size of the ball bearing, the force of the spring, the distance the plunger extends from the housing, and other attributes of the plunger that effect friction between the housing and the outer sleeve.

Further, in some implementations, the driver may be adjusted by drilling or forming one or more holes in select ones of the flat springs. For example, a hole positioned proximate the midpoint of the lengthwise axis of symmetry of a flat spring decreases its angular deflection when torque is applied thereto. Accordingly, selected placement of holes may be employed for adjustment purposes.

BRIEF DESCRIPTION OF THE DRAWINGS

The description below refers to the accompanying drawings, of which.

DETAILED DESCRIPTION OF AN ILLUSTRATIVE EMBODIMENT

Figures 1A, 1B:
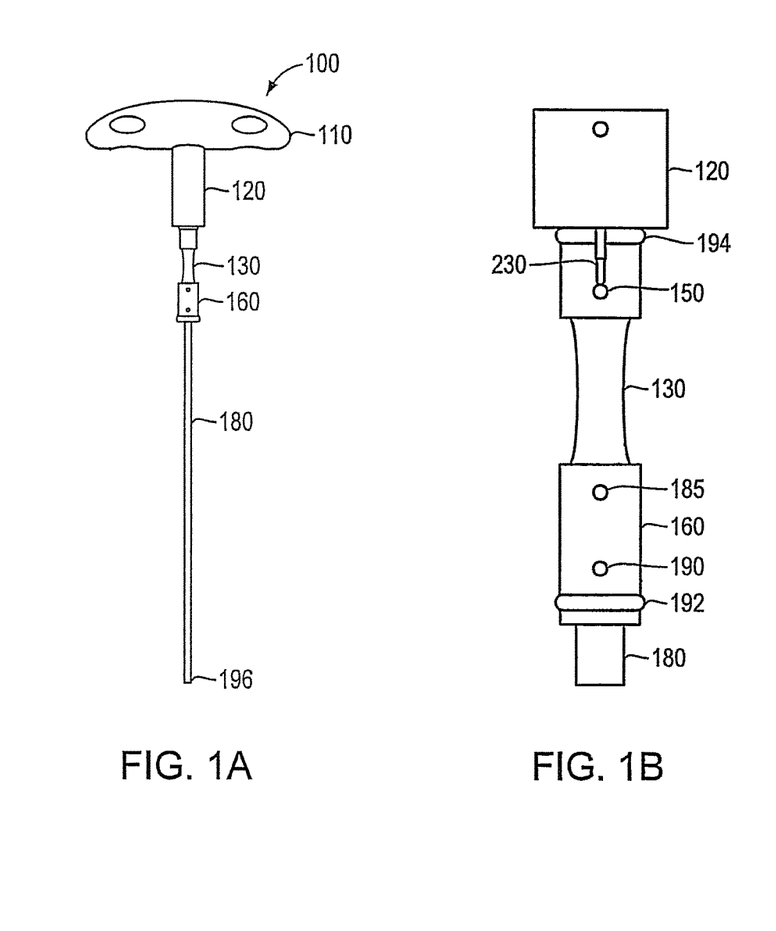
FIG. 1A is a front view of a torque-indicating driver according to an illustrative embodiment of the present disclosure, the driver having an outer sleeve removed to show internal structure.
FIG. 1B is an enlarged front view of a portion of the driver of FIG. 1 with the outer sleeve removed.
Figure 1C:
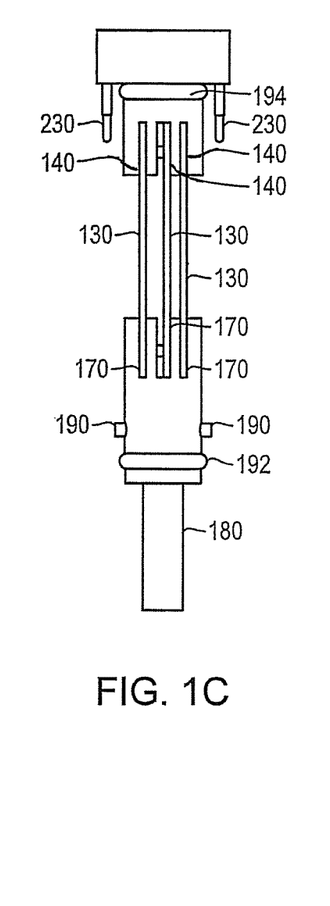
FIG. 1C is an enlarged side view of a portion of the driver of FIG. 1 with the outer sleeve removed.

As shown in FIGS. 1A-1C, a torque-indicating driver 100 according to an illustrative embodiment includes a handle 110 at its proximate end for receiving applied torque. The handle may be a T-handle, a palm-handle, or another type of grip, made from any of a variety of materials including medical grade plastic, stainless-steel, rubber disposed over a metallic frame, or another type of material. The handle is rigidly attached to a cylindrical housing 120, which is in turn coupled to one or more substantially flat torsion springs 130, or simply "flat springs". While in the illustrative embodiment three flat springs 130 are employed, it should be remembered that a different number of flat springs 130, for example, only a single flat spring, may be used in other implementations. The flat springs 130 may engage slots 140 formed in the housing 120, which stabilize the springs and prevent rotation of their proximate ends. One or more fasteners, such as a rivet 150, may pass through the housing 120, rigidly securing the springs 130 in place.

The flat springs 130 are preferably constructed from a flexible material, such as spring steel or spring stainless steel, which may absorb torsional forces, angularly deflecting elastically in response thereto, while not plastically bending or substantially deflecting in other directions. The flat springs 130 employed in the illustrative embodiment are shaped with a concave curvature on each side, which may enhance their ability to angularly deflect without bending in unwanted directions. Alternative implementation, however, may employ flat springs that are differently shaped, for example, substantially rectangular-shaped flat springs.

The flat springs 130 are attached to a hub 160 at their distal ends, for example, by engaging slots 170 arranged in the hub 160. The springs 130 may be retained in the slots 170 by one or more fasteners, for example, a rivet 185. In the illustrative embodiment, the hub 160 is formed as an integral part of a torsion rod 180. However, in alternative implementations, the hub 160 may be rigidly coupled to a separate torsion rod 180. Such coupling may be made in a variety of ways. For example, the torsion rod 180 may extend through a portion of the hub 160 and be fastened to the hub 160 by a pin or screw that prevents the torsion rod 180 from rotating independently of the hub 160. Alternatively, the torsion rod 180 may be welded or otherwise bonded to the hub 160.

The torsion rod 180 may be made from a flexible material, such as spring steel or spring stainless steel, that may angularly deflect elastically in response to torsional forces, while not plastically bending or substantially deflecting in other unwanted directions. In the illustrative embodiment, the torsion rod 180 has a substantially circular cross section. However, in alternative implementations, the torsion rod 180 may have a differing cross-section, for example, it may have a hex-shaped cross section, an octagonal-shaped cross section, an annulus-shaped cross section with a hollow center or some other material disposed at the center, etc. The torsion rod 180 is preferably configured to angularly deflect simultaneous to angular deflection of the flat springs 130, or after the flat springs have already deflected to some degree, to enable measurement of torque by measuring the deflection of the flat springs.

The torsion rod 180 may include a separate, or integrated, bit 196, socket, coupling or other member at its distal tip, for imparting torque upon a load (not show), or for attachment to another member that imparts torque upon a load. As discussed above, one possible use of the torque-indicating driver 100 is to apply torque to a fastener, such as a bone screw or a nut, disposed within the human body. In such an application, the bit 196 may be adapted to fit a head of a particular type of bone screw or the sides of a particular type of nut, and may include features to prevent slippage therefrom.

In contrast to certain prior designs, the driver 100 may have a torsion rod 180 constructed with a quite narrow diameter, allowing the driver 100 to be used in confined spaces, for example, in confined surgical spaces employed in minimally invasive surgery. The flat springs 130 absorbs some torsional forces, such that the torsion rod 180 is subject to moderated forces, even at high torque loads, for example, loads in excess of 14 Nm. It should be apparent however that a differently sized torsion rod 180 may be used and various torque loads achieved.

Figure 2A:
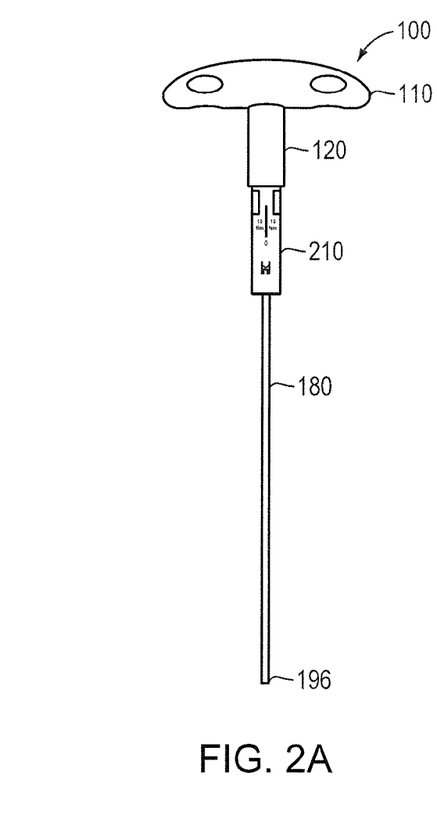
FIG. 2A is a front view of the driver of FIG. 1, with the outer sleeve in place.
Figure 2B:
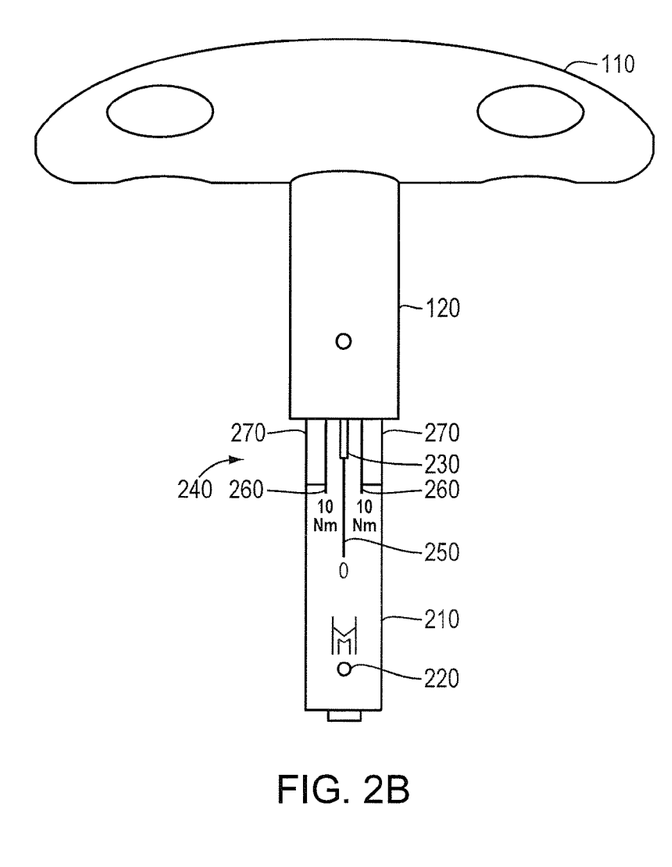
FIG. 2B is an enlarged front view of a portion of the driver of FIG. 1 with the outer sleeve in place.
Figure 2C:
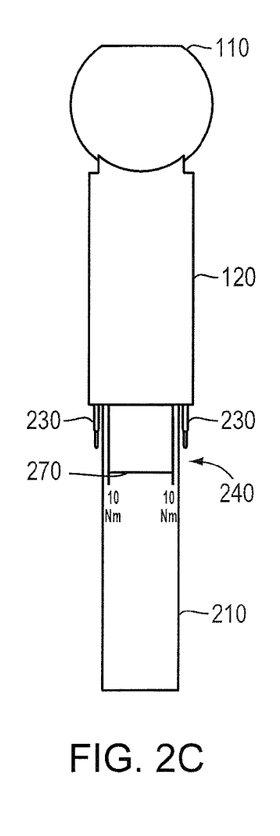
FIG. 2C is an enlarged side view of a portion of the driver of FIG. 1 with the outer sleeve in place.

Referring to FIGS. 2A-2C, the internal structure of the driver 100 is enclosed by a removable outer sleeve 210. When in place, the outer sleeve 210 encloses the hub 160 and extends upwards over the flat springs 130 and a lower portion of the housing 120. The outer sleeve 210 may be supported on the hub 160 by a bushing 192, which may assist in keeping moisture out of the internal structure of the driver. A pin 190 (visible in FIG. 1B and FIG. 1C), which may be spring loaded, may fix the sleeve 210 to the hub 160 by engaging holes 220 or depressions in the outer sleeve 210. Alternatively, the outer sleeve 210 may be rigidly attached to the hub 160 by a fastener, a crimp connection, adhesive, etc.

While the outer sleeve 210 is rigidly attached to the hub 160, it is allowed to freely rotate over the flat springs 130 and the lower portion of the housing 120. In some configurations, an additional bushing 194 is disposed on the lower portion of the housing 120. The bushing 194 may reduce fiction between the outer sleeve 210 and the housing 120, yet provide some stabilization to the proximate end of the upper sleeve 210. The bushing 194 may also keep moisture from entering, protecting the internal structure.

In the illustrative embodiment, a pair of indicators 230 extend downward from the cylindrical housing 120 over portions of the outer sleeve 210. The indicators 230 are disposed on opposing sides of the housing, permitting two-sided viewing. Two sets of torque-indicating markings 240 are likewise etched, painted, or otherwise applied proximate to the indicators 230 on opposing sides of the exterior surface of the outer sleeve 210. The markings 240 may include a centerline 250, which aligns with an indicator 230 when the driver 100 is subject to substantially zero torque, as well as measurement lines 260 that indicate when a particular torque has been achieved. Further, the markings 240 may include warning zones 270, for example, brightly-colored regions arranged to either side of the measurement lines 260 that indicate when a torque limit has been exceeded. High contrast between the indicators 230 and the warning zones 270 may allow a surgeon or other user to easily visually detect excessive torque situations.

In the illustrative embodiment, the measurement lines 260 and warning zones 270 are disposed in pairs, flanking a centerline 250 at an angular distance of about 30 degrees, the approximate limit to which a surgeon or other user may comfortably rotate their hand to apply torque. Such an arrangement permits bidirectional torque measurement, as torque applied in either a clockwise or a counter-clockwise direction may be measured. It should be apparent, however, that the markings 240 may be differently configured depending on the particular implementation of the driver 100. For example, measurement lines 260 may to arranged to only a single side of the centerline 250 to provide only single-direction torque measurement. Alternatively, a greater number of measurement lines 260 may be used to provide finer scale measurement, other types of markings 240 may be used, or some or all markings 240 may be completely absent.

In addition to visual indication provided by markings 240, in some implementations, the torque-indicating driver 100 may provide auditory and/or vibrational feedback to indicate when a particular torque level is reached. In reference to FIGS. 3A-3D, one or more ball-nose spring plungers 310 comprising a ball bearing 320 loaded by a spring 330, and retained by a hold down ring 340, may be disposed in the cylindrical housing 120. A plunger 310 may include threads 350 that engage corresponding threads (not shown) of an opening in the housing 120, or alternatively may be secured by pressure-fitting or another technique.

When disposed in an opening in the housing, the ball bearing 320 of a plunger 310 is arranged to ride about the substantially smooth inner surface of the outer sleeve 210 in response to the driver 100 being subject to torque. The ball bearing 320 is held in contact with the outer sleeve 210 by loading from its spring 330. Holes 360, depressions or other similar structures are arranged at predetermined locations in the sleeve 210. For example, a hole 360 may be positioned inline with each of the measurement lines 260. In such a configuration, when applied torque substantially equals the level indicated by the measurement line 260, the ball bearing 320 encounters the hole 360, and its loading forces it partially therein, such that a spherical cap of the ball bearing 320 becomes disposed in the hole 360. This results in an audible "clicking" noise that may be heard by a surgeon or other user operating the driver 100. In the illustrative embodiment, engagement of the ball bearing 320 and the hole 360 does not substantially lock the housing 120 to the sleeve 210. That is, if torque is decreased, the ball bearing 320 may readily disengage the hole 360, while if torque is increased further, it may also disengage the hole 360. Thus the arrangement provides a torque-indicating, but not torque limiting function.

Figures 3A, 3B:
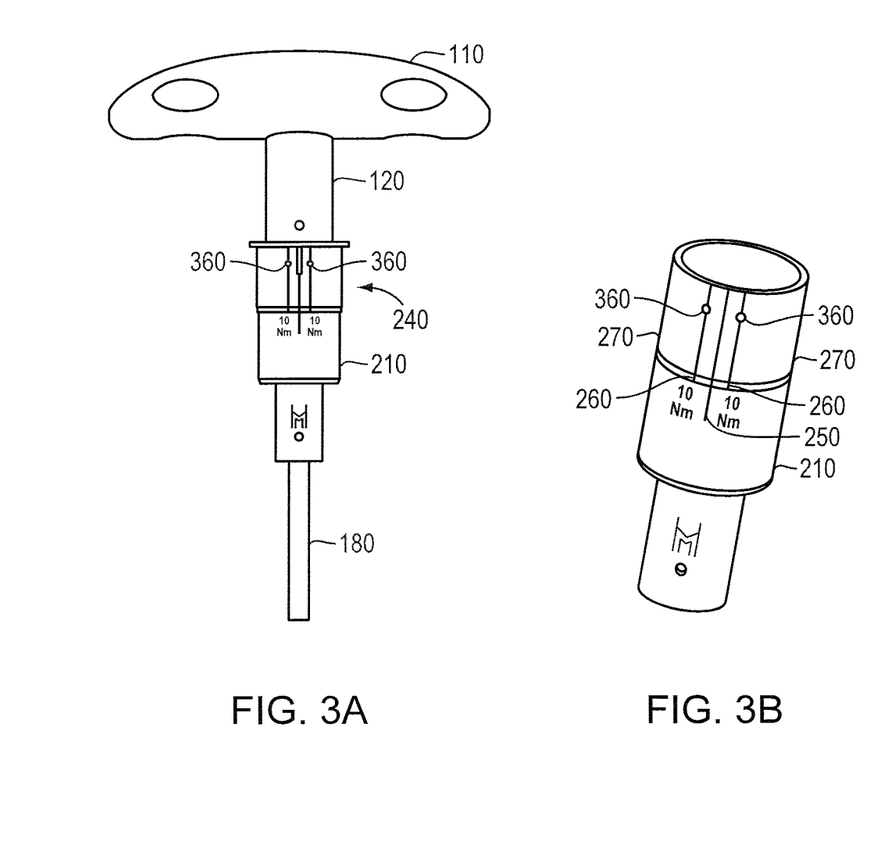
FIG. 3A is a front view of an example implementation that employs one or more ball-nose spring plungers.
FIG. 3B is an isometric view of an outer sleeve for use with the driver of FIG. 3A.
Figure 3C:
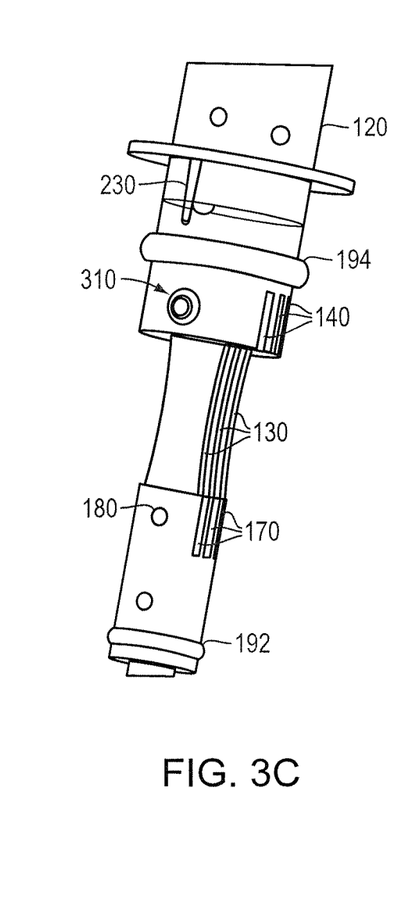
FIG. 3C is an enlarged isometric view of a portion of the driver of FIG. 3A with the outer sleeve removed.
Figure 3D:
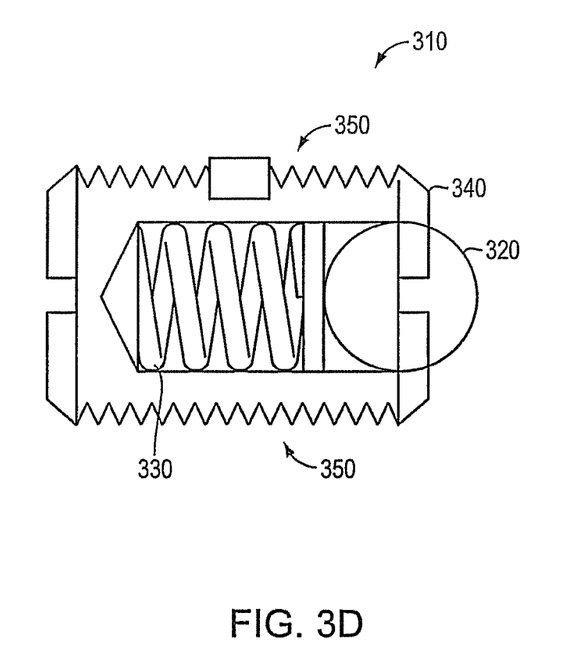
FIG. 3D is a schematic view of an example ball-nose spring plunger that may be used in the implementation of FIGS. 3A-3C.

The volume of the "clicking" noise may be adjusted during design and manufacturing by adjusting the distance the plunger 310 extends from the housing 120, by using a plunger 320 having differing properties, for example, with a spring 330 that exerts increased or decreased force or with a differently sized ball bearing 320, or by other adjustments to the plunger 310 and hole 260 configuration.

In addition to an audible "clicking" noise, a vibration is typically produced when the ball bearing 320 engages the hole 360. Such a vibration is transmitted through the driver 100 to a surgeon or other user holding the handle 110, providing tactile feedback. Tactile feedback may be desirable, especially in environments where ambient noise may reduce the effectiveness of audible feedback and visual indication is insufficient. The degree of vibration may be adjusted by changing the arrangement and/or the type of plunger 310 used, as discussed above.

Further, the one or more plungers 310 may be used to calibrate the driver 100. The size of the ball bearing 320, the force of the spring 330, the distance the plunger 310 extends from the housing 120, and other attributes of the plunger 310 effect friction between the housing 120 and the outer sleeve 210. Increasing or decreasing friction by adjusting or substituting different ball plungers 310 provides differing amounts of resistance between the housing 120 and sleeve 210. This resistance may be used to adjust the torque indicted by the driver 100 when subject to a particular torque load.

Figure 4:
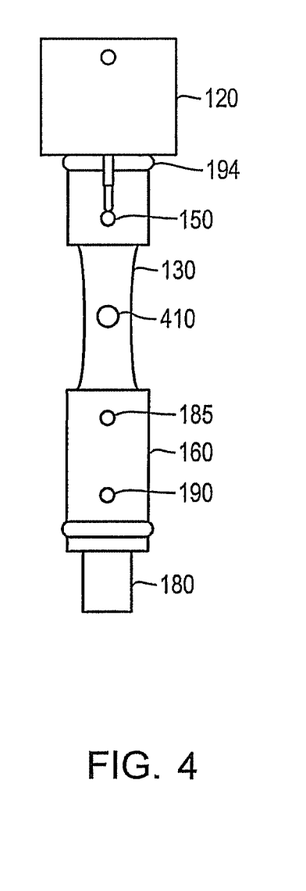
FIG. 4 is a front view of a portion of an example implementation that includes one or more holes disposed through a flat spring.

Further, in some implementations, adjustment or calibration may be made to the torque-indicating driver 100 by drilling or otherwise forming one or more holes in the flat springs 130. In reference to FIG. 4, a substantially circular hole 410 may be positioned proximate to the lengthwise axis of symmetry of one or more of the flat springs 130. It has been found that a hole 410 so positioned decreases the angular deflection of a flat spring 130, rather than increases the angular deflection, when torque is applied thereto. Thus, an implementation with holes may achieve a higher torque limit than an implementation having solid flat springs. The size and placement of holes 410 may be used to increase the torque the flat springs may withstand for adjustment and calibration purposes.

While the above description discusses an illustrative embodiment with some varying implementations, it should be apparent that a number of further modifications and/or additions may be made to the driver 100.

While ball-nose spring plungers 310 are preferred for creating auditory and/or tactile feedback, a variety of other structure may alternatively be employed. For example, a variety of differing types of plungers may be used, including plungers that incorporate differently shaped bearings, such as cylindrical bearings, or other elements in place of bearings, for example, fixed nose elements.

Further, instead of a plunger 310, alternative structures may be employed. For example, a spring-loaded clicker or "cricket" mechanism may be used. Such a cricket may comprise a spring-loaded lever arm with a projection at its tip configured to engage a catch. The lever arm may be secured to the housing 120, and the catch positioned on the interior surface of the outer sleeve 210. Alternatively, the cricket may be disposed between the flat springs 130, such that angular deflection of the flat springs causes a projection on one spring 130 to click upon a catch on another, creating sound and/or tactile sensation. Similarly, sound and or tactile sensation may be electronically created. For example, a sensor, such as a contact sensor an optical sensor, may be triggered when a particular torque level is reached. The sensor may trigger a speaker to produce an audible tone and/or a vibration producing element to provide tactile feedback. Such electronic components may be mounted internal to the housing or otherwise affixed to the driver 100.

Further, while it is above described that the handle 110 is directly attached to the housing 120 via a rigid connection, one or more intermediate elements may be disposed therebetween. For example, a ratcheting mechanism may be used to couple the handle 110 to the housing 120 to allow for ratcheting action.

Further, while it is above described that the indicators 230 are affixed to the housing and the markings 240 are disposed on the outer sleeve, such arrangement may be reversed. For example, an extension of material may project from the outer sleeve 210 over a portion of the housing and function as an indicator 230. Further, an indicator need not include a projection of any type, and may simply be an etched or painted line.

Further, while it is above described that flat springs 130 are couple the housing 120 to the hub 160, other types of torsion springs may be employed. For example, helical torsion springs may be used in place of the flat springs 130, and their angular deflection used to measure torque.

Further, while it is above described that a torsion rod 180 extends from the hub 160, in some alternative embodiments, a substantially inflexible rod may instead be used, which does not angularly deflect in an appreciable manner in response to applied torque.

Further, while repeated reference is made above to use in surgical procedures, for example in minimally invasive surgery, the teachings herein are in no way limited to instruments used for that specific purpose, and may be applicable to instruments used to accomplish a variety of other tasks involving application of torque, in the surgical setting and other settings.

Accordingly, it should be understood that the above descriptions are meant to be taken only by way of example.

What is claimed is:

1. A torque-indicating driver comprising:
   a handle configured to receive applied torque;
   two or more substantially flat torsion springs coupled to the handle, the two or more substantially flat torsion springs constructed from a flexible material configured to angularly deflect elastically in response to the applied torque;
   a housing that couples the two or more substantially flat torsion springs to the handle, the housing having two or more slots that each receive a proximate end of a respective substantially flat torsion spring and prevents rotation of the proximate end with respect to the handle;
   a torsion rod coupled to the two or more substantially flat torsion springs, the torsion rod also constructed from a flexible material configured to angularly deflect elastically in response to the applied torque;
   a coupling that couples the two or more substantially flat torsion springs to the torsion rod, the coupling having two or more slots that each receive a distal end of a respective substantially flat torsion spring and prevents rotation of the distal end with respect to the torsion rod;
   a bit or socket located at a distal end of the torsion rod and configured to impart torque on a load; and
   at least one indicator configured to indicate a torque level imparted on the load.

2. The torque-indicating driver of claim 1 further comprising:
   a first set of torque-indicating markings;
   a second set of torque-indicating markings located on an opposing side of the torque-indicating driver from the first set of torque-indicating markings; and
   wherein the at least one indicator includes a first indicator configured to indicate the torque level in conjunction with the first set of torque-indicating markings, and a second indicator configured to indicate the same torque level in conjunction with the second set of torque-indicating markings.

3. The torque-indicating driver of claim 2 wherein the first indicator and the second indicator both extend over a portion of an outer sleeve that encloses the two or more substantially flat torsion springs, the outer sleeve having the first set of torque-indicating markings and the second set of torque-indicating markings disposed thereon, the first indicator and the second indicator to move with respect to the outer sleeve.

4. The torque-indicating driver of claim 2 wherein at least one of the first set of torque indicating markings and the second sets of torque indicating markings is bidirectional to permit torque measurement in either a clockwise or a counter-clockwise direction.

5. The torque-indicating driver of claim 1 wherein at least some of the two or more substantially flat torsion springs have a hole formed therein, the hole positioned along an axis of symmetry of the substantially flat torsion spring.

6. The torque-indicating driver of claim 1 wherein the load is a bone screw and the bit or socket is configured to engage the bone screw.

7. The torque-indicating driver of claim 1 further comprising:
   a removable outer sleeve that fully encloses the two or more substantially flat torsion springs.

8. The torque-indicating driver of claim 1 wherein the two or more substantially flat torsion springs are shaped with a concave curvature on opposing sides.

9. A torque-indicating driver comprising:
   means for receiving applied torque;
   two or more substantially flat torsion springs coupled to the means for receiving, the two or more substantially flat torsion springs constructed from a flexible material and configured to angularly deflect in response to the applied torque;
   a housing having two or more slots that each receive a proximate end of a respective substantially flat torsion spring and prevent rotation of the proximate end with respect to the means for receiving applied torque;
   a torsion rod coupled to the two or more substantially flat torsion springs, the torsion rod also constructed from a flexible material and configured to angularly deflect in response to the applied torque;

a coupling having two or more slots that each receive a distal end of a respective substantially flat torsion spring and prevent rotation of the distal end with respect to the torsion rod;

means for imparting torque on a load, the means for imparting coupled to the torsion rod; and means for indicating a torque level imparted on the load.

10. The torque-indicating driver of claim 9 wherein the load is a bone screw and the means for imparting torque is configured to engage the bone screw.

11. The torque-indicating driver of claim 9 further comprising:

a first set of torque-indicating markings; and wherein the means for indicating a torque level include a first indicator configured to indicate the torque level in conjunction with the first set of torque-indicating markings.

12. The torque-indicating driver of claim 11 further comprising:

a second set of torque-indicating markings located on an opposing side of the torque-indicating driver from the first set of torque-indicating markings; and wherein the means for indicating a torque level include a second indicator configured to indicate a torque level in conjunction with the second set of torque-indicating markings.

13. The torque-indicating driver of claim 12 wherein the first indicator and the second indicator both extend over a portion of an outer sleeve that encloses the two or more substantially flat torsion springs.

14. The torque-indicating driver of claim 11 wherein the first set of torque indicating markings is bidirectional to permit torque measurement in either a clockwise or a counterclockwise direction.

15. The torque-indicating driver of claim 9 wherein at least some of the two or more substantially flat torsion springs have a hole formed therein, the hole positioned along an axis of symmetry of the spring.

16. The torque-indicating driver of claim 9 further comprising:

a removable outer sleeve that fully encloses the two or more substantially flat torsion springs.

17. The torque-indicating driver of claim 9 wherein the two or more substantially flat torsion springs are shaped with a concave curvature on opposing sides.

* * * * *